United States Patent
Kath et al.

[11] Patent Number: 5,882,601
[45] Date of Patent: Mar. 16, 1999

[54] DEFLECTED SEPTUM SEAL ACCESS PORT

[75] Inventors: Gary S. Kath, Scotch Plains; Lihu Yang, Edison; Gregory W. King, Carteret, all of N.J.

[73] Assignee: Merck & Co., Ltd., Rhaway, N.J.

[21] Appl. No.: 877,986

[22] Filed: Jun. 18, 1997

[51] Int. Cl.⁶ ..................................................... B01L 3/02
[52] U.S. Cl. .................... 422/102; 422/100; 422/101; 422/104; 436/179; 436/180
[58] Field of Search .............. 422/99, 100, 101, 422/102, 104; 436/179, 180, 174

[56] References Cited

U.S. PATENT DOCUMENTS

| | | | |
|---|---|---|---|
| 3,814,079 | 6/1974 | Le Roy, Sr. | 422/102 X |
| 4,015,941 | 4/1977 | Kurata | 422/102 |
| 4,342,724 | 8/1982 | Narra | 422/101 |
| 5,061,450 | 10/1991 | Aoyagi | 422/101 |
| 5,167,929 | 12/1992 | Korf et al. | 422/102 |
| 5,344,036 | 9/1994 | Stanescu et al. | 215/251 |
| 5,720,925 | 2/1998 | Oehme | 422/102 |
| 5,753,508 | 5/1998 | Robertson et al. | 436/2 |

FOREIGN PATENT DOCUMENTS

| | | |
|---|---|---|
| 0 582 383 | 11/1946 | United Kingdom . |
| 0 884 078 | 12/1961 | United Kingdom . |
| 1 267 419 | 3/1972 | United Kingdom . |
| 2 264 702 | 9/1993 | United Kingdom . |
| WO 84/04672 | 12/1984 | WIPO . |
| WO 96/22157 | 7/1996 | WIPO . |
| WO 96/33010 | 10/1996 | WIPO . |
| WO 97/04863 | 2/1997 | WIPO . |

*Primary Examiner*—Harold Y. Pyon
*Attorney, Agent, or Firm*—Dianne Pecoraro; Elliott Korsen; Mark R. Daniel

[57] ABSTRACT

An access port for a reaction or other fluid vessel which maintains the vessel under an inert gas atmosphere and maintains the integrity of the inert gas seal while performing filtered filling or draining operations is presented. The port uses a deflected septum sealing technique. The invention can be used for a number of laboratory and clinical operations on a variety of size and shape vessels. The combination of the appropriate vessel with this access port is very well suited for use in lab automation systems, such as automated solid phase chemical synthesis, biological screening, combinatorial chemistry and other areas where reaction chemistry is conducted.

7 Claims, 4 Drawing Sheets

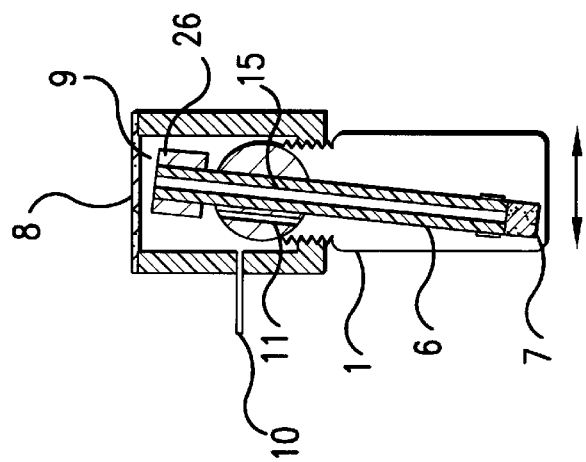
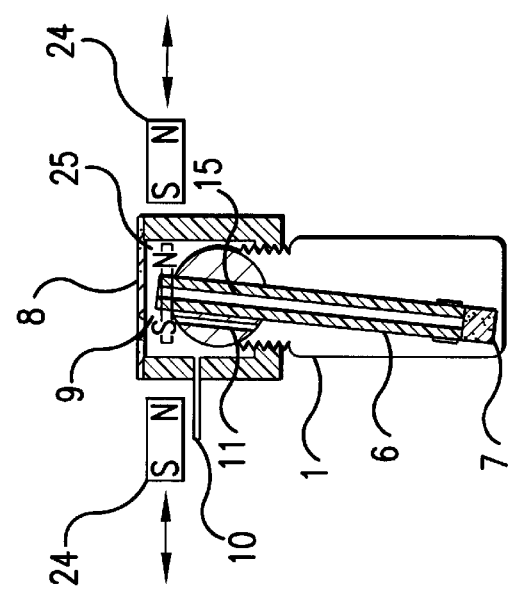
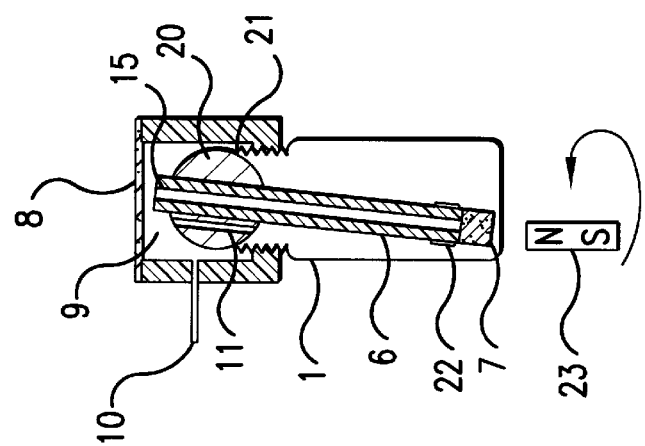

DEFLECTED SEPTUM SEAL ACCESS PORT

BACKGROUND OF THE INVENTION

An access port for a reaction vessel is presented which is useful with solid phase chemical synthesis or other chemistry, clinical or biological fluid handling operations which require a fluid containment vessel which is chemically inert, provides for control of the internal atmosphere and temperature, facilitates mixing, provides for accurate and facile addition of fluids as well as filtered removal of fluid from the vessel and is suitable for automation.

The inlet and outlet ports for fluid addition and removal are a critical features of the design of a reaction vessel, since maintaining the integrity of the inert or reactive atmosphere and retaining any solid support, such as resin inside the vessel, is critical.

In some designs, fluid enters the top of the vessel and drains out the bottom of the vessel through manually operated valves. Solids are maintained inside the vessel by placing a frit at the bottom of the vessel which serves as a filter which passes fluid only. This type of valving arrangement is suitable for a small number of reaction vessels but is impractical for automatic filling and draining of an array of vessels.

One design approach, suitable for automation, is to replace the top valve with a septum and add fluid by piercing the septum with a dispensing canula. The bottom valve may be replaced with a u-tube which will drain the vessel when sufficient head pressure is applied to cause a siphon. However, with this design, the u-tube outlet port can prematurely drain if pressures build up inside the reaction vessel during heating operations. Also, since the outlets feed into a common waste manifold, there is no way to monitor a blockage of the outlet of an individual reaction vessel. This vessel design is expensive to build, difficult to change frits, and require vessels with bottom seals.

In order to overcome the problems associated with the vessels which have been previously reported, a novel vessel should be well suited for automatic filling and draining operations using conventional pipetting equipment or other robotic or automation equipment. In addition, the septum access port should be usable with practically any type and size vessel, including but not limited to test tubes, vials, beakers, flasks, jars and 96-well plate. Further the vessel should not have a bottom drain port since this restricts direct heating and cooling of the vessels and with a smooth bottom, heating and cooling may be effected by direct application of a hot stage or cooling reservoir to the vial. The vessels should operate under an inert atmosphere with no fluid loss. That is, higher inert gas pressures could be used if the top of a sipper tube and the fluid in the vessel always have the same applied pressure. In the event of a leak in the septum due to multiple piercing of an aspirating or dispensing canula, the contents of the vessel should be contained and not leak. Any applied inert or reactive gas should bleed or vent out a predetermined hole, while maintaining the vessel under an inert gas atmosphere and assuring retention of the liquid in the vessel. The optimum design should not have check valves, u-tubes, or o-rings which decrease the reliability and increase the cost of manufacturing arrays of reaction wells. Automatic back flushing of any filtering frits should be provided as this will reduce the chance of frit or filter blockage. The design should also provide for the draining of each vessel individually when used in a multi-vessel array, as this would increase the vacuum capacity available for this operation. Such a device could also permit incorporation of sensors in the aspiration or dispensing canula which would insure an individual vessel was properly drained.

SUMMARY OF THE INVENTION

A reaction vessel system having a deflecting septum seal access port comprising a septum seal and top fill and fritted drain port which permits fluid addition and waste or product removal from a vessel while maintaining a controlled atmosphere within the vessel, over a range of operating pressures and temperatures, is presented. A dual function design where the inlet/outlet port is not only used to fill and drain the vessel but also used to mix the fluid inside the vessel is also presented. The device of the instant invention is applicable for solid phase chemical synthesis as well as any other chemical, clinical, or biological operation where filtering through a frit is necessary. Control of the atmosphere inside the vessel is easily accomplished by maintaining a positive pressure of an inert or reactive gas within the vessel throughout its use.

BRIEF DESCRIPTION OF THE INVENTION

FIG. 3 is a cross-sectional side view of a dual purpose deflected septum inlet/outlet port which also serves as a mixer via swirling action via magnetic coupling.

FIG. 4 is a cross-sectional side view of a dual purpose inlet/outlet deflected septum port which also serves as a mixer via swirling action via top drive coupling.

FIG. 5 is a cross-sectional side view of a dual purpose deflected septum inlet/outlet port which also serves as a mixer via swirling action via momentum coupling.

DETAILED DESCRIPTION OF THE INVENTION

A reaction vial system having a deflecting septum seal access port comprising a septum seal and top fill and fritted drain port which permits fluid addition and waste or product removal from a vessel while maintaining a controlled atmosphere within the vessel, over a range of operating pressures and temperatures, is presented. A dual function design where the inlet/outlet port is not only used to fill and drain the vessel but also used to mix the fluid inside the vessel is also presented. The device of the instant invention is applicable for solid phase chemical synthesis as well as any other chemical, clinical, or biological operation where filtering through a frit is necessary. Control of the atmosphere inside the vessel is provided by maintaining a positive pressure of an inert or reactive gas throughout its use.

The deflected septum seal access port comprises a cap which is sized to securely fit a vessel; the size and composition of the vessel being chosen based on the desired chemical or biological process to be conducted; the cap having an inside and outside, the inside of the cap being exposed to the inside of the vessel, the outside of the cap being exposed to the environment outside the vessel; the cap having a centrally located hole which permits ingress and egress of materials to and from the vessel through the hole; a sipper tube connected to the inside of the cap and extending from inside the cap towards the bottom of the vessel, the sipper tube having an integral frit or filter; a septum sheet being placed across the top of the cap and covering the hole in the cap to provide a barrier between the contents of the vessel and the atmosphere outside the vessel, the septum sheet being maintained in place by an over cap, a weight or some pressure means which maintain positive pressure on the cap and prevent the septum sheet from moving during entrance or removal of material from the vessel; the cap further having an inlet port and vent hole which communicate the inside of the vessel with the environment outside the vessel; the cap may also be constructed to provide a pipetting means stop, the stop being positioned to limit the travel of the pipetting means into the vessel so that as the pipetting means is inserted into the sipper tube, the pipetting means stop deflects the septum sheet against the top of the sipper tube causing the septum sheet to become pressed between the pipetting means stop and the top of the sipper tube forming a seal between the pipetting means and sipper tube, such that as fluid is removed from or dispensed into the vessel, the deflected septum seal insures the fluid flows through the sipper tube into the vessel; the vent hole providing a means for escape of gas from vessel during addition of liquid to the vessel and the inlet port providing a means for introducing air, inert or reactant gas useful during the reaction sequence.

Figure 1:
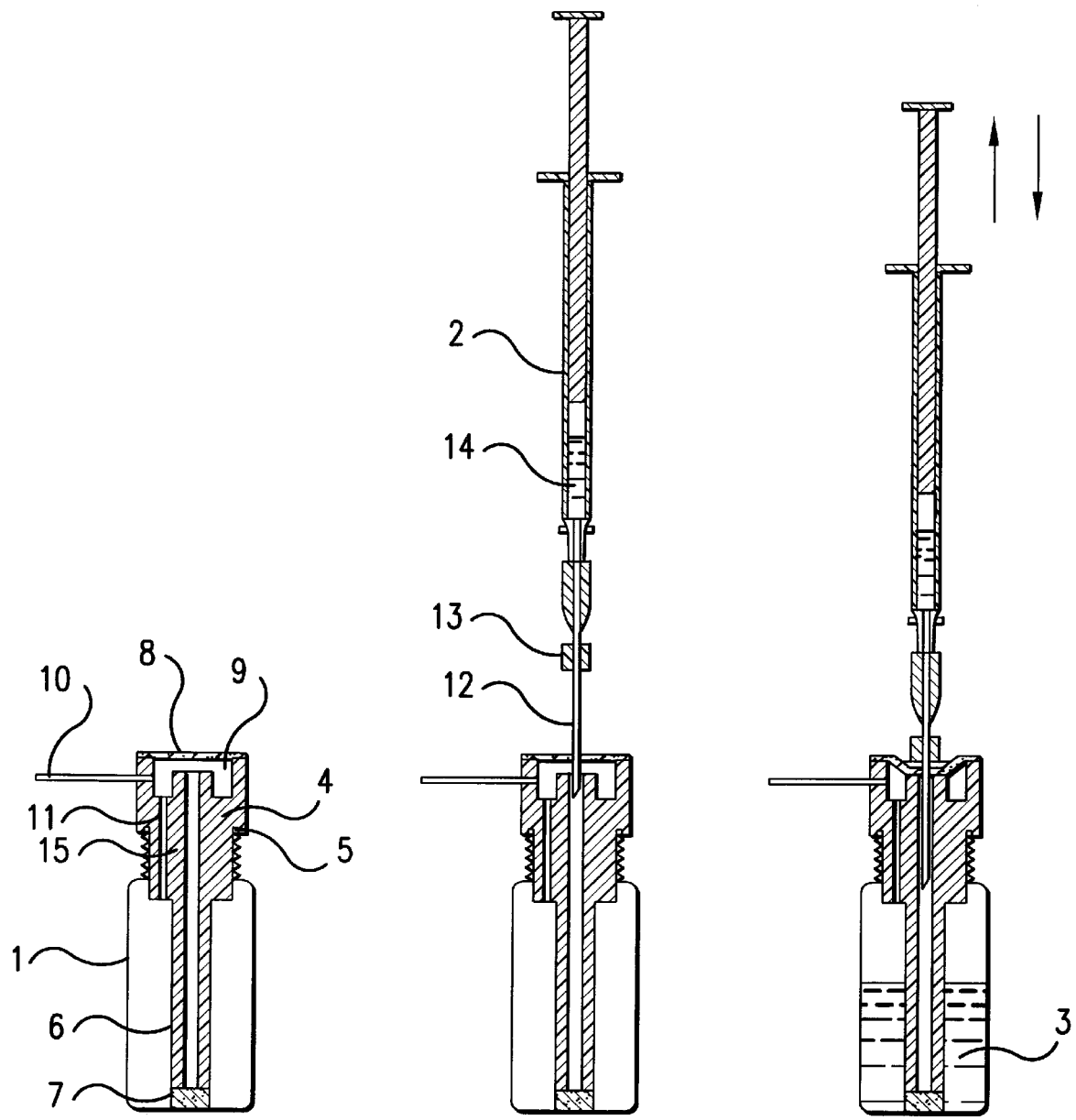
FIGS. 1A–1C are a cross-sectional side view of a single reaction vessel and a method of dispensing and aspirating fluid into the vessel.

One embodiment of the deflected septum seal access port of the present invention is illustrated in FIGS. 1A–1C. The figure shows a single vessel (1) being filled or drained using a manually or automatically positioned syringe (2). The invention consists of a chemically suitable vessel (1) which may contains fluid or fluid and solid mixtures (3). A screw or press fit cap (4) is placed on the vessel and sealed with a flexible seal (5). Connected to the cap is a sipper tube (6), with an integral frit or filter (7). The sipper tube (6) extends from inside the top of the cap to the inside bottom of the vessel. Across the top of the cap (4) is placed a septum sheet (8). A set of clamps which hold the septum sheet (8) in place during operation are not shown.

By "chemically suitable vessel" is meant a vessel which will not be attacked, solubilized, softened or otherwise interacted with by the reagents, solvents, solids, products or other components which are either added to the vessel or produced during a reaction sequence. The "chemically suitable vessel" composition is also chosen to assure that reactants, products or by-products of the reaction are not absorbed, adsorbed or otherwise trapped by the composition. Suitable compositions for such vessels are well known in the art, and include such compositions as glass, TEFLON, polyethylene and other materials which are suited for laboratory experimentation.

By "flexible seal" is meant materials such as gaskets, o-rings or other devices which are known in the art to effect a tight junction between a cap and a container.

By "septum sheet" is meant a piece of material such as silicon rubber, natural rubber, TEFLON coated elastomer or other material known to function as a septum, which is cut or molded to the dimensions of the inside of the cap and which serves as a septum for the top of the vessel.

When material is not being removed from or added to the vessel, there exists a gap (9) between the bottom of the septum sheet (8) and the top of the sipper tube (15). When in use, air, inert or reactant gas enters into inlet port (10) which is positioned to permit the gas to be applied to the top of the sipper tube (15). In addition, the gas can flow through vent hole (11) to blanket the top of the fluid or fluid and solid mixture (3) inside the reaction vessel (1).

To fill the vessel, (1) a manually or automatically positioned syringe canula (12) is position above the septum and lowered while piercing through the septum (8). The canula (12) has a canula stop (13) which contacts the septum (8) as the canula (12) is inserted into the sipper tube (6). The canula stop deflects the septum (8) against the top of the sipper tube (15) in a manner such that the septum (8) is squeezed between the canula stop (13) and the top of the sipper tube (15) forming a seal between the syringe canula (12) and sipper tube (6).

As fluid (14) is dispensed into the vessel (1), the deflected septum (8) seal insures fluid (14) only flows through the sipper tube (6) and frit or filter (7) into the vessel (1). As liquid is dispensed into the vessel (1), back pressure gas can vent through the vent hole (11). When the syringe canula (12) is withdrawn from the vessel (1), the top of the sipper tube (15) is exposed to the inert gas due to the gap (9) which exists between the bottom of the septum (8) and the top of the sipper tube (15). Since the top of the sipper tube (15) and top of the liquid inside the vessel are exposed to the same gas pressure, the system will not leak and can be operated over a range of pressures and temperatures.

One means of draining the vessel (1) or of removing product from the vessel, is to use a syringe canula (12) which is inserted into the septum (8) at a depth where the canula stop (13) deflects the septum (8) and makes a seal between the syringe canula (12) and the top of the sipper tube (6). As the syringe (2) aspirates the fluid, a positive pressure is applied to the top of the fluid by gas flow from the gas inlet port (10) through the vent hole (11).

Figure 2:
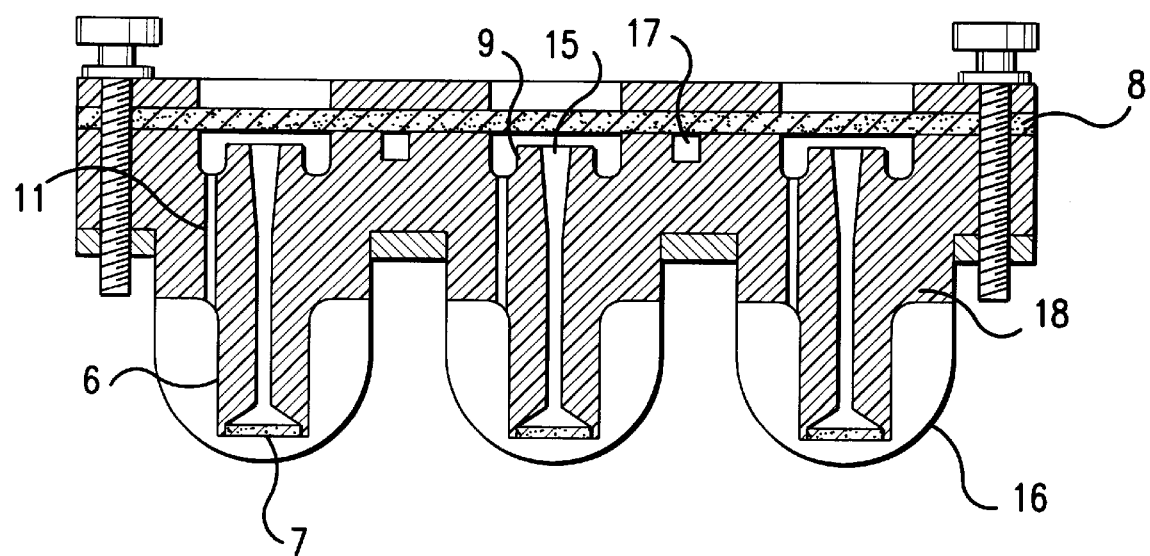
FIG. 2 is a cross-sectional side view of a 3×3 array of reaction vessels.

The deflected septum seal access port can be configured in multi-dimensional arrays which provide a means of performing many more studies within a limited amount of space. FIG. 2 presents a cross-sectional view of the deflected septum seal applied to a 3×3 array of reaction vessels. In this arrangement, vessel cups (16) are used to hold the liquid/solid mixture. In the embodiment shown in the drawing, an array of fritted sipper tubes (6) is machined or molded out of a single piece of plastic. This single block containing the array is fitted to a complimentary set of vessels which may simply be an array of discrete cavities drilled from a single block of plastic or other suitable material. Once a septum sheet is laid across the top of the fritted sipper tube array and is clamped in position, each vessel may be individually used for a separate reaction sequence. The top of the sipper tube (15) is recessed slightly below the bottom the septum sheet (8). Channels (17) cut in the housing permit application of air, inert or reactant gas beneath the septum sheet (8) and into the cavity or vessel(18) at the top of the sipper tube (15) as well as the top of the fluid inside the vessels via the vent hole (11). In an other embodiment of this invention, the fritted sipper tubes (6) are made of more than one piece, the pieces are either welded, pressed, screwed or otherwise attached prior to use.

FIG. 3 exemplifies yet an other embodiment of this invention in which the sipper tube (6) is used to fill or drain the vessel (1) as well as mix the contents of the vessel (1). In this embodiment, the sipper tube (6) extends through a ball bearing (20) which is free to swivel on the neck of the reaction vessel (21). As the sipper tube (6) is rocked back and forth or through a conical rotational movement it imparts mixing into the liquid contained in the vessel. The sipper tube movement is initiated and maintained through any of a number of means. For example, a Teflon coated ferromagnetic tube (22) may be placed around the sipper tube (6) and impart a force on the sipper tube (6) via magnetic coupling to a moving magnet (23) outside the vessel. Depending on the movement pattern of the magnet (23), the sipper tube (6) can be made to rock or swivel in a manner to mix the fluid inside the vessel. A seal to the top of the sipper tube (15) is again made by piercing the septum sheet (8) and squeezing it against the top of the sipper tube (15) via a canula stop (13) attached to a syringe canula (12).

Another means of driving the sipper tube (6) is shown in FIG. 4. In this arrangement the sipper tube (6) again is free to swivel about the neck of the vessel (21) on the ball bearing (20). External magnets (24) move back and forth outside the vessel imparting force to a plate (25) loosely coupled to the top of the sipper tube (15). This causes the sipper tube (6) to rock and the contents of the vessel to mix.

Still another embodiment for mixing the contents of the vessel using the sipper tube is shown in FIG. 5. In this embodiment, a weight (26) is placed above the ball bearing (20) and moves the vessel (1) back and forth. The mass and momentum of the weight (26) will cause the sipper tube (6) to rock back and forth mixing fluid inside the vessel (1).

Figure 6:
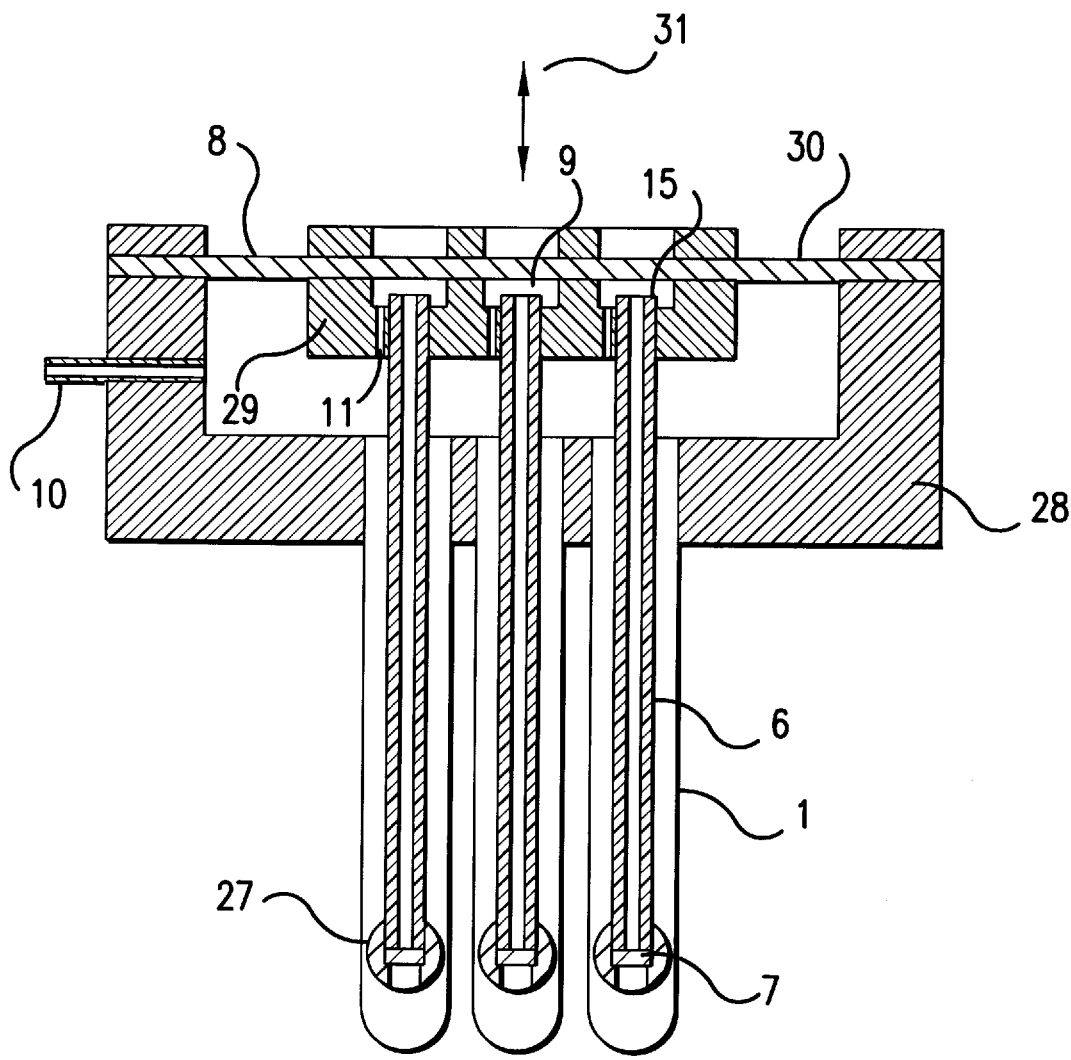
FIG. 6 is a cross-sectional side view of a 3×3 array of reaction vessels with dual purpose deflected septum inlet/outlet ports which also serves as a mixer via plunger action.

Still another embodiment which provides for mixing using the sipper tube (6), is shown in FIG. 6. In this embodiment, the sipper tube (6) acts as a plunger. A plunger (27) is simply constructed by increasing the diameter of the sipper tube (6) at some point along the sipper tube. In this arrangement, if the sipper tubes (6) and the array of the vessels (1) can move up and down relative to one another, the plungers (27) will move through the liquid and mix the fluid. The sipper tube's frit or filter (7) is positioned near the bottom of the vessel during aspirating operations. To maintain a seal between the top of the vessel housing (28) and the top of the sipper tube housing (29), the flexible seal (30), is formed by pressing the flexible septum sheet against the top of the sipper tube. To impart force into the sipper tube housing (29) a simple external force (31) is applied via an air cylinder, linear drive or other drive mechanism known in the art. The force (31) will cause the sippers (6) and plungers (27) to move relative to the vessels (1) causing fluid to stream around the plungers (27) and mix the fluid.

Other means of mixing with the sipper tube are included within the scope of this invention and include spinning the sipper tube, vibrating the sipper tube, the use of sonic waves to mix the solution, rotating the vial and using heat to generate convection currents which mix the solution.

A further embodiment of this invention provides for the introduction to and removal from the vial of material without a fixed vent tube, wherein venting is accomplished using a separate venting canula which acts in cooperation with the transfer canula. In this embodiment, a flexible septum sheet is aligned above a sipper tube. The flexible septum sheet is again pressed against the top of the sipper tube when material is to be withdrawn or introduced by way of a transfer canula, however venting is accomplished through the use of a second venting canula which may be adjacent to the transfer canula. The venting canula may be vented to the ambient atmosphere or in the alternative, vacuum, inert gas or reactant gas may be added thorough this canula. Additionally, the venting canula may be useful for the introduction of liquids, solids and suspensions where filtration is not desired.

What is claimed is:

1. A deflected septum seal access port which permits fluid addition and waste or product removal from a vessel while maintaining an inert or reactive gas atmosphere within the vessel comprising: a cap which is sized to securely fit a vessel; the size and composition of the vessel being chosen based on the desired chemical or biological process to be conducted; the cap having an inside and outside, the inside of the cap being exposed to the inside of the vessel, the outside of the cap being exposed to the environment outside the vessel; the cap having a centrally located hole which permits ingress and egress of materials to and from the vessel through the hole; a sipper tube connected to the inside of the cap and extending from inside the cap towards the bottom of the vessel, the sipper tube having an integral frit or filter; a septum sheet being placed across the top of the cap and covering the hole in the cap to provide a barrier between the contents of the vessel and the atmosphere outside the vessel, the septum sheet being maintained in place by an over cap, a weight or some pressure means which maintain positive pressure on the cap and prevent the septum sheet from moving during entrance or removal of material from the vessel; the cap further having an inlet port and vent hole which communicate the inside of the vessel with the environment outside the vessel; the cap can also be constructed to provide a canula stop, the stop being positioned to limit the travel of the canula into the vessel so that as the canula is inserted into the sipper tube, the canula stop deflects the septum sheet against the top of the sipper tube causing the septum sheet to become pressed between the canula stop and the top of the sipper tube forming a seal between the canula and sipper tube, such that as fluid is removed from or dispensed into the vessel, the deflected septum seal insures the fluid flows through the sipper tube into the vessel; the vent hole providing a means for escape of gas from vessel during addition of liquid to the vessel and the inlet port providing a means for introducing air, inert or reactant gas useful during the reaction sequence.

2. The deflected septum seal access port of claim 1, wherein venting is accomplished using a separate venting canula which acts in cooperation with a transfer canula.

3. The port of claim 1, wherein the sipper tube functions as a mixing means.

4. The mixing means of claim 3, wherein the sipper tube is plunger shaped and moves in an up and down, motion relative to the vessel.

5. The mixing means of claim 3, wherein a coated ferromagnetic tube is placed around the sipper tube and imparts a force on the sipper tube via magnetic coupling to a moving magnet outside the vessel.

6. The mixing means of claim 3, wherein the sipper tube is inserted through a ball bearing which is free to swivel on the top of the vessel such that when motion is imparted to the sipper tube, mixing is imparted to the contents of the vessel.

7. The mixing means of claim 6, wherein the sipper tube and ball bearing are weighted with an external weight such that when the vessel is moved the mass and momentum of the external weight cause the sipper tube to mix the fluid inside the vessel.

* * * * *